United States Patent
Jacotin (10) Patent No.: US 9,435,753 B2
(45) Date of Patent: Sep. 6, 2016

(54) METHOD OF NON-DESTRUCTIVE INSPECTION AND A DEVICE FOR IMPLEMENTING THE METHOD

(75) Inventor: Yves Jacotin, Houilles (FR)

(73) Assignee: SNECMA, Paris (FR)

( * ) Notice: Subject to any disclaimer, the term of this patent is extended or adjusted under 35 U.S.C. 154(b) by 483 days.

(21) Appl. No.: 13/699,389

(22) PCT Filed: May 17, 2011

(86) PCT No.: PCT/FR2011/051108
§ 371 (c)(1),
(2), (4) Date: Nov. 21, 2012

(87) PCT Pub. No.: WO2011/148079
PCT Pub. Date: Dec. 1, 2011

(65) Prior Publication Data
US 2013/0070897 A1    Mar. 21, 2013

(30) Foreign Application Priority Data

May 28, 2010 (FR) ...................................... 10 54181

(51) Int. Cl.
*G01N 23/04* (2006.01)
*G01N 23/18* (2006.01)

(52) U.S. Cl.
CPC .............. *G01N 23/04* (2013.01); *G01N 23/18* (2013.01)

(58) Field of Classification Search
CPC ............................... G01N 23/04; G01N 23/18
See application file for complete search history.

(56) References Cited

U.S. PATENT DOCUMENTS

| | | |
|---|---|---|
| 2,900,513 A | 8/1959 | Duffy |
| 3,755,672 A | 8/1973 | Edholm et al. |
| 4,497,062 A | 1/1985 | Mistretta et al. |
| 4,761,558 A | 8/1988 | Schulz |
| 6,295,335 B1 | 9/2001 | Cossard |
| 6,435,715 B1* | 8/2002 | Betz et al. ..................... 378/197 |
| 2002/0032927 A1* | 3/2002 | Dinkler ............... A61B 6/0442 5/601 |
| 2003/0095633 A1 | 5/2003 | Van Woezik |
| 2006/0079764 A1* | 4/2006 | Wright et al. ................ 600/431 |

(Continued)

FOREIGN PATENT DOCUMENTS

| | | |
|---|---|---|
| EP | 1 014 078 | 6/2000 |
| WO | 02 103338 | 12/2002 |

OTHER PUBLICATIONS

Chen, L. et al., "Feasibility of volume-of-interest (VOI) scanning technique in cone beam breast CT-a preliminary study," Medical Physics, vol. 35, No. 8, pp. 3482 to 3490, (Jul. 8, 2008), XP012116177.

(Continued)

*Primary Examiner* — Nicole Ippolito
*Assistant Examiner* — Sean Luck
(74) *Attorney, Agent, or Firm* — Oblon, McClelland, Maier & Neustadt, L.L.P.

(57) ABSTRACT

A method of non-destructively inspecting a mechanical part includes directing high energy electromagnetic radiation emitted by a source onto the part for inspection and picking up the radiation that has passed through the part. A mask that absorbs the radiation is interposed between the source and the mechanical part and includes at least one opening in alignment with the source and a given zone for inspection of the part, a shape and dimensions of the opening being determined so that only the given zone for inspection of the part is exposed to the electromagnetic radiation.

12 Claims, 5 Drawing Sheets

(56) References Cited

U.S. PATENT DOCUMENTS

| | | | |
|---|---|---|---|
| 2008/0029500 A1* | 2/2008 | Malley et al. | 219/121.85 |
| 2009/0180106 A1* | 7/2009 | Friedrich et al. | 356/138 |
| 2009/0232282 A1* | 9/2009 | Belson et al. | 378/203 |
| 2009/0256078 A1* | 10/2009 | Mazin | 250/362 |
| 2010/0034357 A1* | 2/2010 | Svesson et al. | 378/152 |
| 2010/0046697 A1* | 2/2010 | Balakin | 378/21 |

OTHER PUBLICATIONS

International Search Report Issued Aug. 24, 2011 in PCT/FR11/51108 Filed May 17, 2011.

* cited by examiner

METHOD OF NON-DESTRUCTIVE INSPECTION AND A DEVICE FOR IMPLEMENTING THE METHOD

The present invention relates to a method of non-destructive inspection of a mechanical part, such as a turbine blade, by causing high energy electromagnetic radiation to be transmitted through the part, and the invention also relates to a device for implementing the method.

Among the various known techniques for non-destructive inspection, there is the technique of directing high energy electromagnetic radiation, such as X-rays, towards a part for inspection and in recovering the radiation that emerges therefrom by means of a detector in order to form an image representative of the interaction between the electromagnetic radiation and the internal structure of the part for inspection, thus making it possible to reveal the presence or absence of defects in the part.

Nevertheless, in that technique, the radiation emitted by the source impacts against all of the part for inspection and is diffused by the surroundings of the part and by the internal structure of said part, thereby leading to diffuse zones and to a loss of contrast in the resulting images that prevents the presence of defects being detected.

That drawback is particularly significant when inspecting hollow blades such as the blades of a turbine stage of a turbine engine. Such blades present an internal three-dimensional structure that is complex and they also have a thermally protective coating that leads to a large amount of the radiation being diffused inside the blades.

In order to reduce those difficulties, proposals have been made to place filter means such as a plate of beryllium between the source of electromagnetic radiation and the part for inspection so as to eliminate the low energy components of the incident radiation, which components form a large part of the diffuse radiation.

It is also known to place an absorbent mask around the part for inspection so as to limit or eliminate radiation diffused by the surroundings of the part.

Nevertheless, neither of those two solutions is found to be satisfactory since with the first solution not only are the filter means insufficient for eliminating all of the radiation diffused by the internal structure of the part, but they also lead to a loss of contrast and of detection sensitivity by eliminating a fraction of the incident radiation, while in the second solution, the mask is ineffective against radiation diffused by the internal structure of the part.

A particular object of the invention is to provide a solution to those problems that is simple, effective, and inexpensive.

To this end, the invention provides a method of non-destructive inspection of a mechanical part, such as a turbine blade in particular, the method consisting in directing high energy electromagnetic radiation emitted by a suitable source onto the part for inspection, in picking up the radiation that has passed through the part, and in forming an image of the part from the radiation that is picked up, the method being characterized in that it consists in interposing a mask between the source and the mechanical part, the mask being of material that is suitable for absorbing the electromagnetic radiation and that has an opening, and in aligning the opening with the source and a given zone for inspection of the part, the shape and the dimensions of the opening being determined so that only said zone for inspection of the part is exposed to the electromagnetic radiation.

According to the invention, the mask is arranged between the electromagnetic radiation source and the part for inspection and it allows the incident radiation to pass only towards a certain zone for inspection of the part, thereby enabling optimum detection sensitivity to be obtained, since this zone receives all of the energy components of the emitted radiation.

The shape and the dimensions of the opening in the mask are determined relative to the shape and the dimensions of the zone for inspection of the part, thereby avoiding other portions of the part being exposed to the incident radiation and preventing diffuse radiation being formed inside the part by those other portions.

The mask may be positioned at any distance from the source and from the part, it merely being necessary for the shape and the dimensions of the opening to be adapted appropriately for limiting exposure to the given zone for inspection, as mentioned above.

According to another characteristic of the invention, the shape of the opening in the mask corresponds to the projection of the outlines of the given zone for inspection onto a plane perpendicular to the axis of the beam emitted by the source, and the dimensions of the shape of the opening are then determined by applying a scaling ratio that is a function of the axial position of the mask relative to the mechanical part and the source.

Advantageously, the edges of the opening are in alignment with the peripheral rays of the beam emitted by the source so as to avoid the incident radiation being diffused by the edges of the opening.

According to another characteristic of the invention, the absorbent mask is made in the form of a lead plate of a thickness that depends on the nature of the electromagnetic radiation.

The electromagnetic source may be an X-ray source, in which case the thickness of the lead plate is about 8 millimeters (mm), or else it may be a gamma ray source in which case the lead plate presents a thickness greater than 8 mm, because of the strong power of gamma rays to penetrate through the material.

The invention also provides a device for implementing the method as described above, the device comprising means for supporting and positioning the absorbent mask, means for supporting and positioning the mechanical part, and means for aligning the opening in the mask and the zone for inspection of the mechanical part with the radiation source.

In a first embodiment of the device of the invention, the support and positioning means comprise a hinged robot arm suitable for taking hold of a mechanical part in order to place a given zone of said mechanical part in an inspection position.

Advantageously, the support and positioning means comprise a table movably mounted relative to the stationary source and having a plurality of housings for absorbent masks so as to bring each mask in succession into alignment with the source and a given zone for inspection of the part.

In this embodiment, the robot arm takes hold of a part and orients it in a predetermined position for observing a given zone of the mechanical part, and then the table is moved to put a mask corresponding to the given zone for observation into alignment with the source and said given zone. Thereafter, electromagnetic radiation is emitted and an image is acquired. The above-mentioned operations are repeated in order to perform non-destructive inspection of a plurality of zones of the part using different masks of shapes and dimensions that are adapted to observing those zones.

In a second embodiment of the invention, the support and positioning means comprise a structure having first and second stages superposed along the axis of the electromagnetic beam, the second stage being arranged between the first stage and the source and including at least one location for receiving an absorbent mask in alignment on the axis of the beam with at least one location for a parts support of the first stage.

According to another characteristic of the invention, the structure is movable in translation along an axis perpendicular to the axis of the beam, and each of the first and second stages includes a plurality of the above-mentioned locations in alignment along said perpendicular translation axis.

Advantageously, each support mounted in a location of the first stage includes projections for positioning at least one mechanical part for inspecting a given zone of the mechanical part.

In this second embodiment, the operator places at least one part on the support, with the projections of the support enabling a given zone for inspection of the part to be put in a predetermined orientation, the support then being mounted in a location of the first stage. The mask having an opening adapted to exposing the given zone is mounted in the location of the second stage that is in alignment with the axis of the beam. The part is then exposed to radiation and an image of the given zone is obtained.

The structure is then moved along its translation axis so as to bring a location of the first stage and a location of the second stage onto the axis of the beam of electromagnetic radiation and the above operations are repeated with a different support and a different mask suitable for observing another given zone of the mechanical part.

The invention can be better understood and other details, advantages, and characteristics of the invention appear on reading the following description made by way of non-limiting example and with reference to the accompanying drawings, in which.

Figure 1:
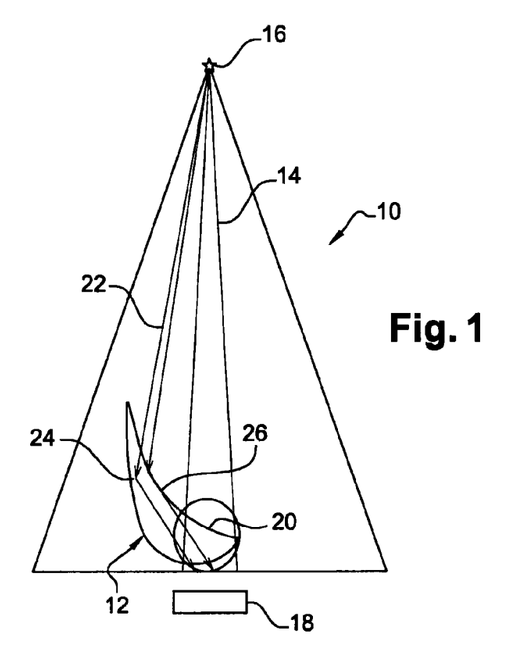
FIG. 1 is a diagrammatic view of a prior art device for non-destructive inspection by emitting electromagnetic radiation.

Reference is made initially to FIG. 1, which shows a device 10 for inspecting a mechanical part 12 by transmitting electromagnetic radiation 14 through the part 12. The device 10 has a source 16 of high energy electromagnetic radiation, i.e. radiation capable of passing through the mechanical part 12. The mechanical part 12 is placed facing the source 16 in the beam that it emits. A detector 18 is in alignment with the source 16 and the part 12, and it is arranged on the opposite side of the part 12 remote from the source 16 so as to receive the radiation transmitted through the mechanical part 12. A gray-scale image is thus obtained and it represents the attenuation of the radiation on passing through the mechanical part 12. With such an image, it is possible in principle to detect the presence or the absence of defects in the part 12 relative to a reference image.

Nevertheless, that device 10 is not satisfactory since the incident radiation is not limited to the zone 20 for inspection, and some of the incident radiation 22 emitted by the source 16 interacts with other zones 24 of the part 12, thereby generating radiation 26 that is diffused inside the part 12, which radiation is in addition to the radiation diffused by the zone for inspection, thereby leading to fuzzy zones being formed in the images that are obtained and reducing sensitivity for detecting defects.

In addition to the diffusion of the incident radiation by the internal structure of the part 12, it is also possible for the surroundings of the part to diffuse radiation, thereby leading to further degradation of the resulting images.

This is particularly true with turbine blades 12 having a three-dimensional internal shape that is complex, as mentioned above. As a result, the inspection of critical zones, such as the leading edges of blades or the roots of blades, for example, cannot be performed in satisfactory manner.

Figure 2:
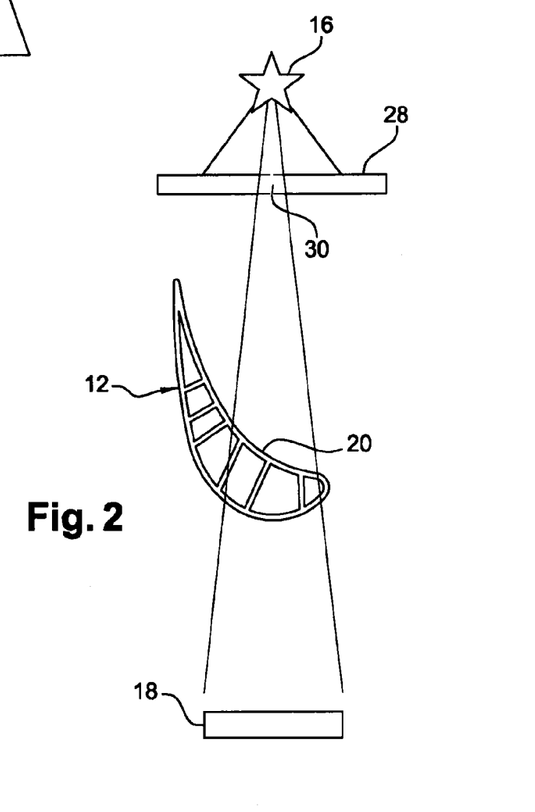
FIG. 2 is a diagrammatic view of the non-destructive method of the invention for inspection by emitting electromagnetic radiation.

The invention provides a solution to this problem by interposing a mask 28 that absorbs the electromagnetic radiation between the part 12 for inspection and the radiation source, the mask having an opening 30 for passing a fraction of the incident radiation without absorption towards a given zone 20 for inspection of the mechanical part 12. The shape and the dimensions of the opening are determined relative to the given zone for inspection in such a manner that only said zone for inspection is exposed to the electromagnetic radiation when the opening is in alignment with the source of radiation and the zone for inspection (FIG. 2).

With such a method, no radiation is diffused by the other zones of the part or by the surroundings of the part, thereby enabling contrast to be increased in the images of the zones that are exposed to the radiation and thus improving the sensitivity with which defects are detected.

In practical manner, the shape of the opening in the mask corresponds to the projection of the outlines of the given zone for inspection onto a plane perpendicular to the axis of the beam emitted by the source, and the dimensions of the shape of the opening are then determined by applying a scaling ratio that is a function of the axial position of the mask 28 relative to the mechanical part 12 and to the source 16.

Figure 3:
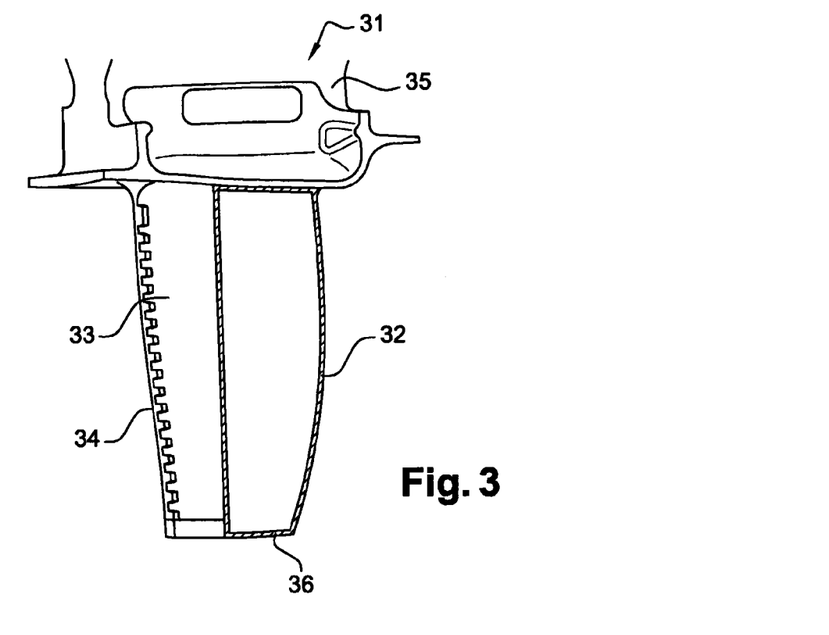
FIG. 3 shows a turbine blade of a turbine engine and the given zone corresponds to the leading edge which is the only zone exposed to the electromagnetic radiation.
Figure 4:
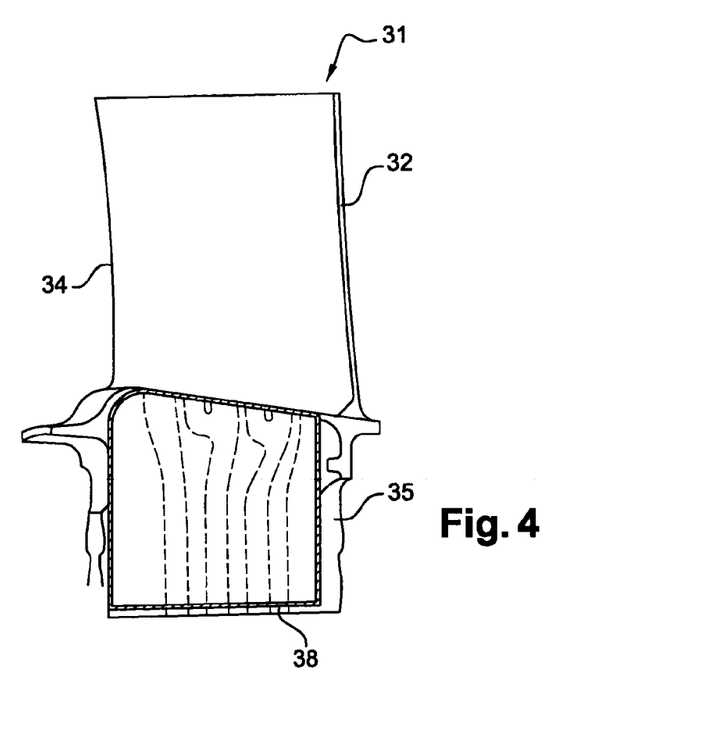
FIG. 4 also shows a turbine blade, the given zone that is exposed to the electromagnetic radiation corresponding to the root of the blade.

FIG. 3 shows a turbine blade 31 of a turbine engine, the blade comprising an airfoil 33 connected to a root 35. The airfoil 33 has a leading edge 32 and a trailing edge 34. By using the method of the invention, it is possible for exposure to the electromagnetic radiation to occur on only an upstream portion of the blade including the leading edge (portion 36 outlined in shaded lines in FIG. 3), or indeed on only a portion of the blade root (portion 38 outlined in shaded lines in FIG. 4), with this being done by using a mask having an opening of the same shape as the given zone 36 or 38 for inspection, except that the dimensions of the opening 30 in the mask 28 are reduced by a scale factor as a function of the position of the mask 28 between the source 16 and the mechanical part 12.

In the description below, two devices for implementing the method of the invention are described. Each of these devices includes means for supporting and positioning the absorbent mask, means for supporting and positioning the mechanical part, and means for aligning the opening in the mask and the zone for inspection of the mechanical part with the radiation source.

Figure 5:
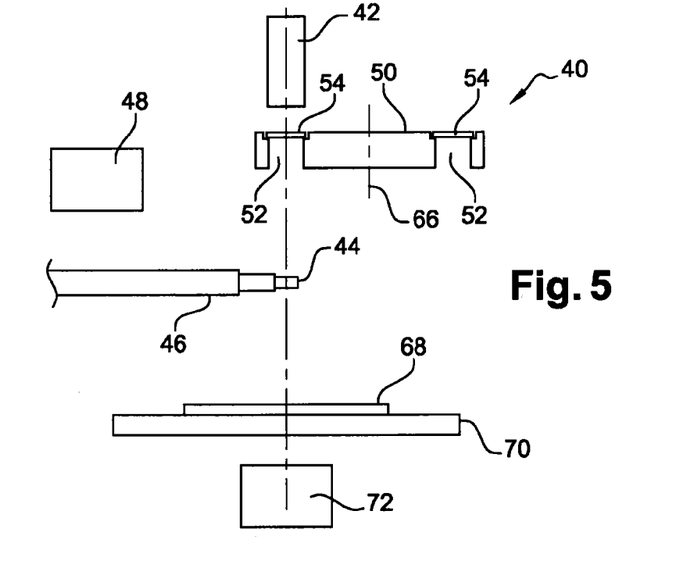
FIG. 5 is a diagrammatic view of a device for implementing the method of the invention.
Figure 6:
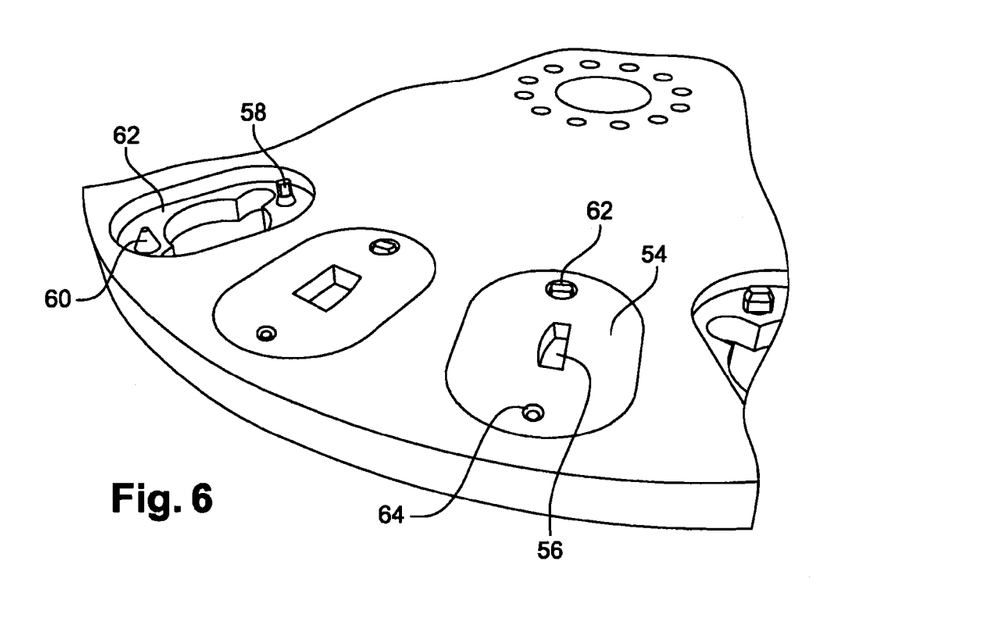
FIG. 6 is a perspective view of a mask-supporting turntable used with the FIG. 5 device.

In a first embodiment shown in FIGS. 5 and 6, the device 40 has a stationary source 42 emitting electromagnetic radiation towards a mechanical part 44 carried by a hinged robot arm 46 suitable for taking hold of a mechanical part, e.g. stored in a magazine 48 situated nearby (FIG. 5). The robot arm 46 has six degrees of freedom so as to enable any zone of the mechanical part 44 to be placed facing the radiation source 42.

A circular turntable 50 is mounted between the radiation source 42 and the mechanical part 44 and has a plurality of recessed housings 52 arranged in a circle at its outer periphery (FIG. 6). Each housing 52 is for receiving a flat absorbent mask 54 having a single opening 56.

Each housing 52 includes keying means for use when installing the absorbent mask 54. These keying means comprise two rods 58 and 60 formed on an internal rim 62 of a housing 52 and extending towards the source 42, one of the rods (58) being of square section and the other rod (60) being of tapering shape. The two keying rods 58 and 60 are received in corresponding orifices 62 and 64 of the mask 50 so as to guarantee that the mask 50 is correctly installed in its housing 52 and thus that the opening 56 of each mask 50 is positioned in a known predetermined position designed to pass the electromagnetic radiation towards a given zone for inspection of a part.

The turntable 50 is mounted to turn about an axis 66 relative to the stationary source 42 so that turning the turntable 50 brings the opening in each of the masks 54 in succession into alignment with the source 42 and a given zone for inspection of a mechanical part.

An image intensifier 68 is mounted on a support 70 and serves to convert the high energy electromagnetic radiation transmitted through the part 44 into light radiation that is picked up by a camera 72.

The device 40 is used as follows in order to implement the method of the invention. Firstly, the robot arm 46 is controlled so as to take hold of a mechanical part 44 in the magazine 48 and bring a given zone for inspection, e.g. the blade root, into a determined orientation facing the source. The turntable 50 is turned about its axis 66 so as to bring the opening of a mask 54 corresponding to the blade root into alignment with the source 42 and the blade root. The source 42 is then caused to emit high energy electromagnetic radiation, a fraction of which is absorbed by the mask 54 while the remainder passes through the opening in the mask 54 and impacts the blade root. The transmitted radiation is then converted by the image intensifier 68 and is then picked up by the camera 72.

In order to inspect the leading edge portion of the blade, it suffices to change the orientation of the part 44 so that this zone faces the source 42. The turntable 50 is turned so that the mask 54 corresponding to observing the leading edge portion is in alignment with the source 42 and the part 44, and a new acquisition is performed.

In this device, the opening of a mask 54 is aligned with a given zone for inspection of a mechanical part essentially by means of the hinged robot arm 46 making use of its six degrees of freedom, with the turntable 50 serving to position the mask in register with the source 42.

FIGS. 7 to 10 show a second device 68 for implementing the method of the invention.

Figure 7:
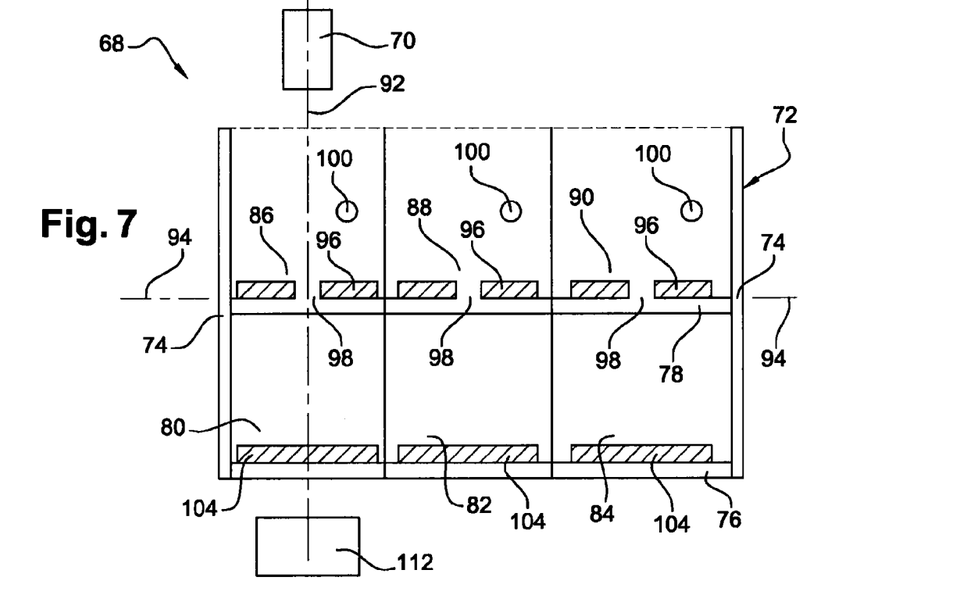
FIGS. 7 and 8 show another device for implementing the method of the invention.
Figure 8:
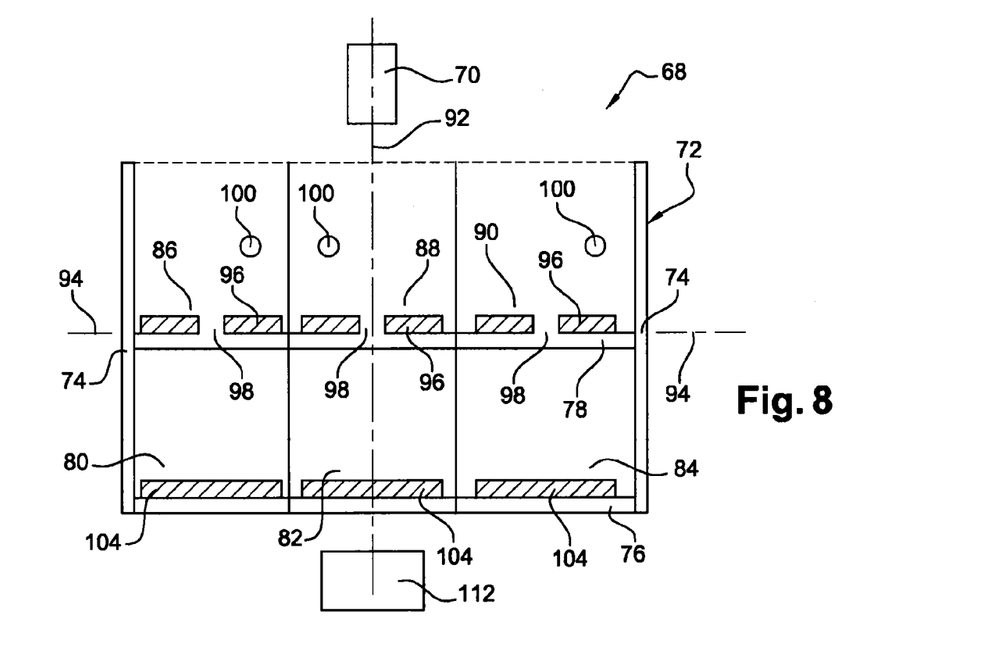

This second device 68 has a high energy electromagnetic radiation source 70 arranged above a structure 72 having uprights 74 supporting a first stage 76 and a second stage 78 that are superposed along the axis of the beam. The second stage 78 is arranged between the first stage 76 and the radiation source 70. Each stage has three locations 80, 82, and 84, or 86, 88, and 90. The locations in the first and second stages are positioned in such a manner that a location of the first stage is in alignment on the axis 92 of the beam with a location of the second stage. The locations in each stage are also in alignment along an axis 94 perpendicular to the beam axis 92, the axis 94 defining an axis along which the structure 72 can be moved.

Figure 9:
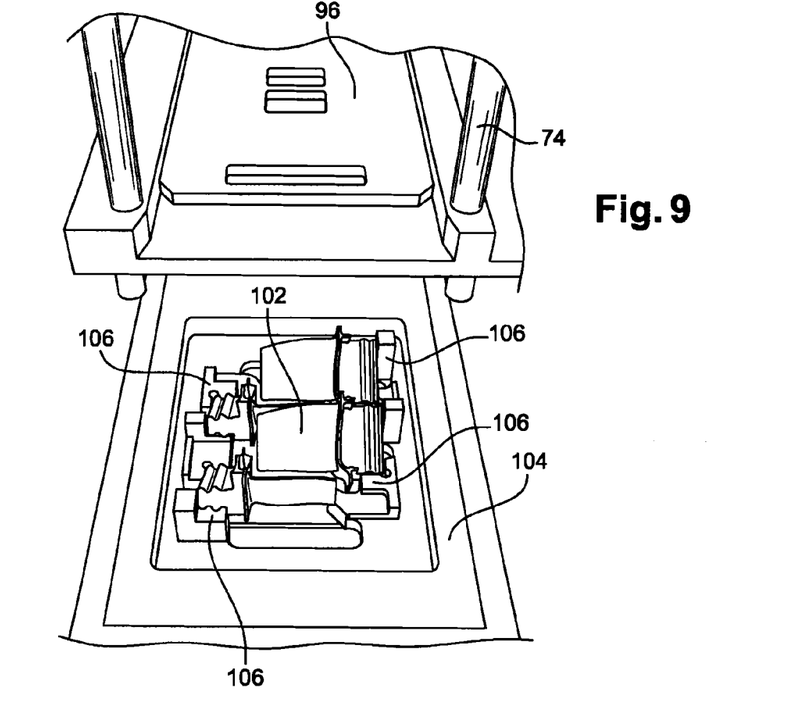
FIG. 9 shows a parts support for use with the device of FIGS. 7 and 8.
Figure 10:
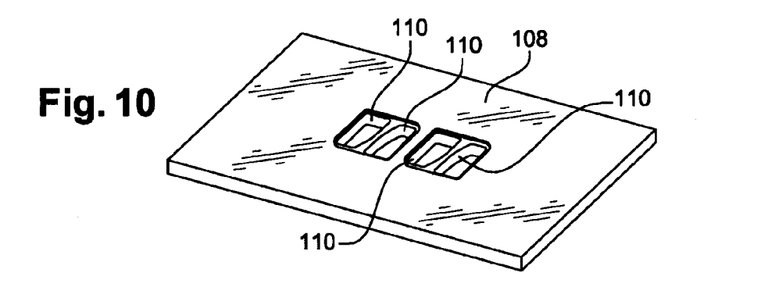
FIG. 10 is a diagrammatic perspective view of a mask used with the device of FIGS. 7 and 8.

Each of the locations 86, 88, and 90 of the second stage 78 is for receiving an absorbent mask 96 in the form of a plate having at least one opening 98 (FIG. 9). Each absorbent mask 96 is engaged axially in a location 86, 88, or 90 of the second stage 78 on an axis 100 that is perpendicular both to the axis 92 of the electromagnetic beam and the axis 94 in which the structure 72 is moved in translation.

The parts 102 for inspection are mounted in supports 104 having projections 106 for positioning a given zone of each part 102 in a position in which said given zone is in alignment with an opening 98 of a mask 96 and with the source 70 (FIGS. 7 and 9).

Each support 104 for a part is engaged by being moved in translation along the axis 100 into a location 80, 82, or 84 of the first stage 76.

Abutment means (not shown) are provided at the rear ends of the locations 80, 82, 84, 86, 88, and 90 in the first and second stages 76 and 78, and they serve to provide indexing along the axis 100 for each mask 96 relative to the associated support 104 for a part, and thus perform indexing along the axis 100 of the openings 98 in each of the masks 96 relative to the given zones for inspection of the parts 102 mounted in the associated supports 104.

The parts supports 104 and the masks 96 are dimensions in such a manner as to be received in their respective locations without slack along the travel axis 94 of the structure so as to provide indexing along this axis 94 of the openings 98 in the masks 96 of the second stage 78 relative to the given zones for inspection of the parts 102 mounted in the supports 104 of the first stage 76.

When used in combination with the projections 106 of the supports 104, these indexing means serve to ensure accurate alignment of the openings 98 in the masks 96 of the second stage 78 with the given zones for inspection of the parts on the first stage 76.

Although not shown in the figures of this second device, keying means may also be provided to prevent the masks 96 and the parts supports 104 being wrongly mounted in their respective locations.

In a particular embodiment, a first mask 108 has four openings 110 adapted to observing leading edge portions of four turbine blades, and a first parts support has projections adapted to positioning the leading edge portions of four different blades. Thus, when the mask 108 is engaged in a location 86 of the second stage 78 and the support is engaged in the associated location 80 of the first stage 76, each of the openings 110 in the mask 108 is in alignment with a leading edge portion of a different blade. Thereafter, a high energy electromagnetic beam is emitted and generates radiation that is transmitted simultaneously through the four leading edge portions of the four blades, the transmitted radiation being picked up by a receiver 112 (FIGS. 7 and 8).

This second device 68 thus presents the advantage relative to the first device of enabling given zones to be inspected simultaneously in a plurality of parts, thereby reducing the time needed for inspecting those parts.

Thereafter, in order to inspect other zones of these blades simultaneously, it suffices to position the blades in a second support having projections provided for this purpose and then to engage the second support carrying the repositioned blades in the location 82 of the first stage 76, with the associated location 88 of the second stage 78 then including a mask having four openings appropriate for exposing only those other zones to the electromagnetic radiation. The structure 72 is then moved in translation along the axis 94 to bring the source 70 of electromagnetic radiation into alignment with the openings in the second mask and with those other zones of the blades on the second support (FIG. 8).

It is not difficult for an operator to move the blades manually into a second support, and that avoids any need for the operator to handle the absorbent masks which are very heavy, these masks remaining in position in their respective locations.

By way of example, the parts supports used in the second device may be molded out of resin.

The absorbent masks 54, 96, or 110 may be made of lead and they are about 8 mm thick when the electromagnetic radiation is X-rays. Other radiation sources may be used, and in particular a gamma ray source. Under such circumstances, the masks 54, 96, or 110 are thicker, being about 15 mm thick, given the high penetration power of this type of radiation.

The lead masks are advantageously covered in a fine layer of aluminum so as to avoid the operators who handle the masks being contaminated with lead. Nevertheless, the edges of the openings are not provided with aluminum in order to avoid diffuse radiation being formed by the edges of the openings.

Figure 11:
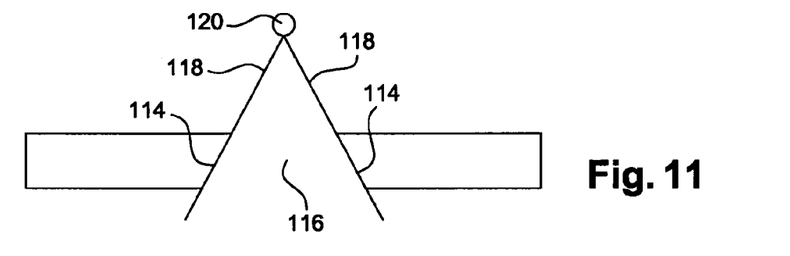
FIG. 11 is a diagrammatic view of the edges of an opening in an absorbent mask used in the method of the invention.

In order to avoid any radiation being diffused by the edges 114 of a mask opening, it is desirable for the edges 114 of the opening 116 to be in alignment with the peripheral rays 118 of the beam emitted by the source 120, as shown diagrammatically in FIG. 11.

The invention may be used in combination with an absorbent mask of the prior art mounted around the mechanical part.

The invention claimed is:

1. A device for non-destructive inspection of a mechanical part, comprising:
    a source suitable for emitting a high energy electromagnetic beam in a direction;
    a mask of material that is suitable for absorbing the electromagnetic beam and comprising an opening, the shape and the dimensions of the opening being determined so that only a given zone for inspection of the part is exposed to the electromagnetic beam; and
    a structure which supports and positions the mask and the mechanical part, the structure including first and second stages superposed along an axis of the electromagnetic beam extending in a vertical direction, the second stage being arranged between the first stage and the source,
    wherein the second stage includes at least one location which receives the mask, and the first stage includes a support for the part such that the mask at the second stage is in alignment along the axis of the beam with the support of the first stage,
    wherein the first and second stages are fixed in the structure such that a distance between the first stage and the second stage along the axis of the beam is constant, and
    wherein the first and second stages are movable together in translation in a horizontal direction along a same single translation axis.

2. A device according to claim 1, wherein each of the first and second stages includes a plurality of the at least one locations in alignment along said translation axis.

3. A device according to claim 1, wherein each support mounted in a location of the first stage includes projections for positioning at least one mechanical part for inspecting a given zone of the mechanical part.

4. A device according to one of claim 3, wherein the opening being aligned with the part for inspection of the mechanical part, the shape of the opening in the mask corresponds to the projection of the outlines of the given zone for inspection onto a plane perpendicular to the axis of the beam emitted by the source, and the dimensions of the shape of the opening are then determined by applying a scaling ratio that is a function of the axial position of the mask relative to the mechanical part and the source.

5. A device according to claim 1, wherein edges of the opening are in alignment with peripheral rays of the beam emitted by the source.

6. A device according to claim 1, wherein the absorbent mask is made in the form of a plate of a thickness that depends on the nature of the electromagnetic beam.

7. A device according to claim 1, wherein the source of electromagnetic beam is an X-ray source or a gamma ray source.

8. A device according to claim 1, wherein another mask suitable for absorbing the electromagnetic beam is arranged around the mechanical part.

9. A device according to claim 1, wherein the mechanical part is a turbine blade.

10. A device according to claim 3, wherein the mechanical part is a turbine blade, and the projections are configured to cooperate with a root of the turbine blade.

11. A device according to claim 1, wherein the structure includes uprights supporting the first and second stages, the uprights extending in a direction along the axis of the beam.

12. A device according to claim 2, wherein the first stage includes the plurality of the locations for receiving parts, and the second stage includes the plurality of locations for receiving masks.

* * * * *